US007961967B2

(12) United States Patent
Yoshida et al.

(10) Patent No.: US 7,961,967 B2
(45) Date of Patent: Jun. 14, 2011

(54) ADAPTIVE DENSITY MAPPING IN COMPUTED TOMOGRAPHIC IMAGES

(75) Inventors: Hiroyuki Yoshida, Watertown, MA (US); Janne Näppi, Boston, MA (US); Michael E. Zalis, Newtonville, MA (US); Wenli Cai, Dorchester, MA (US)

(73) Assignee: The General Hospital Corporation, Boston, MA (US)

( * ) Notice: Subject to any disclaimer, the term of this patent is extended or adjusted under 35 U.S.C. 154(b) by 1023 days.

(21) Appl. No.: 11/607,195

(22) Filed: Nov. 30, 2006

(65) Prior Publication Data

US 2007/0127804 A1    Jun. 7, 2007

Related U.S. Application Data

(60) Provisional application No. 60/741,103, filed on Nov. 30, 2005.

(51) Int. Cl.
*G06K 9/40*    (2006.01)
(52) U.S. Cl. .......................... 382/254; 382/131
(58) Field of Classification Search ............. 250/363.04; 345/424; 348/E5.088, E9.042; 378/4–27, 378/82, 87, 901; 382/131, 254
See application file for complete search history.

(56) References Cited

U.S. PATENT DOCUMENTS

| | | | | |
|---|---|---|---|---|
| 5,647,018 A * | 7/1997 | Benjamin | ..................... | 382/128 |
| 5,920,319 A * | 7/1999 | Vining et al. | .................. | 345/420 |
| 6,331,116 B1 | 12/2001 | Kaufman et al. | ............. | 434/262 |
| 6,343,936 B1 | 2/2002 | Kaufman et al. | ............. | 434/262 |
| 6,366,800 B1 * | 4/2002 | Vining et al. | .................. | 600/425 |
| 7,226,410 B2 | 6/2007 | Long | | |
| 7,596,256 B1 | 9/2009 | Arie et al. | | |
| 2003/0095695 A1 * | 5/2003 | Arnold | .......................... | 382/131 |
| 2004/0114790 A1 * | 6/2004 | Yamamoto et al. | ........... | 382/131 |
| 2004/0136584 A1 | 7/2004 | Acar et al. | ..................... | 382/131 |
| 2004/0167400 A1 * | 8/2004 | Kaufman | ...................... | 600/431 |
| 2005/0152588 A1 | 7/2005 | Yoshida et al. | ............... | 382/128 |
| 2006/0094961 A1 * | 5/2006 | Mikheev et al. | .............. | 600/437 |
| 2007/0116346 A1 | 5/2007 | Peterson et al. | | |
| 2008/0055308 A1 * | 3/2008 | Dekel et al. | ................... | 345/421 |
| 2008/0273781 A1 * | 11/2008 | Manduca et al. | ............. | 382/131 |

FOREIGN PATENT DOCUMENTS

| WO | WO 03/034176 | 4/2003 |
|---|---|---|
| WO | WO 2004/075117 | 9/2004 |
| WO | WO 2005/101314 | 10/2005 |

OTHER PUBLICATIONS

Harbir Singh1, Michael Crawford,2, John Curtin2, and Reyer Zwiggelaar1, 2004, Springer-Verlag Berlin Heidelberg, [online], [retrieved on Mar. 8, 2010]. Retrieved from the Internet:<URL:http://www.springerlink.com/content/ynv4wuyy74mha5g5/fulltext.pdf>.*

(Continued)

*Primary Examiner* — Bhavesh M Mehta
*Assistant Examiner* — Gregory F Cunningham
(74) *Attorney, Agent, or Firm* — Quarles & Brady LLP

(57) ABSTRACT

An adaptive density mapping (ADM) method and system automatically identify interface regions between air and material tagged with contrast agents in computed tomographic (CT) image data, then map CT attenuations of voxels outside the identified interface regions, such that voxels that represent tagged material are made to represent air or another gas.

7 Claims, 8 Drawing Sheets

OTHER PUBLICATIONS

Eduard Groller et al., Virtual Endoscopy for Preoperative Planning and Training of Endonasal Transsphenoidal Pituitary Surgery, May 2005, [online], [Retrieved on Mar. 8, 2010]. Retreived from the Internet:<URL:http://medvis.vrvis.at/fileadmin/publications/PhD_Neubauer.pdf>.*

Michael E. Zalis*, James Perumpillichira, and Peter F. Hahn, "Digital Subtraction Bowel Cleansing for CT Colonography Using Morphological and Linear Filtration Methods", IEEE Transactions on Medical Imaging, vol. 23, No. 11, Nov. 2004, pp. 1335-1343.*

Zigang Wang1, Xiang Li1,2, Lihong Li1,3, Bin Li1, Daria Eremina4, Hongbing Lu5, and Zhengrong Liang1,6,7, "An Improved Electronic Colon Cleansing Method for Detection of Polyps by Virtual Colonoscopy", Sep. 1-4, 2005, Proceedings of the 2005 IEEE Engineering in Medicine and Biology 27th Annual Conference Shanghai, China, 6512-6515.*

Ming Wan, et al., "Automatic Centerline Extraction for Virtual Colonoscopy," *IEEE Transactions on Medical Imaging*, vol. 21, No. 12, Dec. 2002, pp. 1450-1460.

Nappi, J., et al., "Region-Based Supine-Prone Correspondence for the Reduction of False-Positive CAD Polyp Candidates for CT Colonography," *Academic Radiology*, vol. 12, No. 6, Jun. 2005, pp. 695-707.

International Search Report; Dated Apr. 5, 2007; received Apr. 9, 2007; PCT/US2006/046044.

Wenli Cai, et al. "Digital Bowel Cleansing for Computer-Aided Detection for Polyps in Fecal-Tagging CT Colongraphy," *Medical Imaging*, vol. 6144, Mar. 10, 2006, pp. 614422-1-614422-9.

Dongqing Chen, et al., "A Novel Approach to Extract Colon Lumen for CT Images for Virtual Colonoscopy," *IEEE Transactions on Medical Imaging*, vol. 19, No. 12, Dec. 2000, pp. 1220-1226.

Dongqing Chen, et al., "Electronic Colon Cleansing of Colonic Material Tagging and Image Segmentation for Polyp Detection: Detection Model and Method Evaluation," *Nuclear Science Symposium Conference Record*, vol. 3, Oct. 25, 2000, pp. 18131-18125.

Sarong Lakare, et al., "3D Digital Cleansing Using Segmentation Rays," *Proceedings Visualization*, Oct. 8, 2000, pp. 37-44.

Zalis, M., et al., "CT Colonography: Digital Subtraction Bowel Cleansing with Mucosal Reconstruction—Initial Observations," *Radiology*, vol. 226, No. 3, Mar. 2003, pp. 911-917.

Zalis, M., et al., "Digital Subtraction Bowel Cleansing for CT Colonography Using Morphological and Linear Filtration Methods," *IEEE Transactions on Medical Imaging*, Vo. 23, No. 11, Nov. 2004, pp. 1335-1343.

Zigang Wang, et al., "An Improved Electronic Colon Cleansing Method for Detection of Polyps of Virtual Colonoscopy," *Engineering n Medicine and Biology Society*, Sep. 1, 2005, pp. 6512-6515.

International Search Report; Dated Apr. 27, 2007; Rcv'd May 1, 2007; PCT/US2006/045789.

International Search Report; Dated Apr. 27, 2007; Rcv'd May 1, 2007; PCT/US2006/045803.

*International Preliminary Report on Patentability*; Dated Dec. 27, 2007; PCT/US2006/045789, 11 pages.

*International Preliminary Report on Patentability*; Dated Jun. 3, 2008; PCT/US2006/045803, 7 pages.

*International Preliminary Report on Patentability*; Dated Nov. 27, 2007; PCT/US2006/046044, 13 pages.

Article 34 Amendment and Demand, dated Sep. 28, 2007, 25 pages.

Article 34 Amendment and Demand, dated Oct. 2, 2007, 31 pages.

Sethian, "Level Set Methods and Fast Marching Methods", *Cambridge University Press*, 2d edition, ISBN 0521645573, 1999 (Front matter only), 1999, 8 pages.

Frimmel, et al., "Fast and robust method to compute colon centerline in CT colonography," *Proceedings of SPIE*, vol. 5031, 2003, pp. 381-387.

Nappi, et al. "Automated Knowledge-Guided Segmentation of Colonic Walls for Computerized Detection of Polyps in CT Colonography," *Journal of Computer Assisted Tomography*, Jul./Aug. 2002, vol. 26, Issue 4, pp. 493-504.

Frimmel, et al., "Centerline-based colon segmentation for CT colonography," *Med. Phys.*, 32 (8), Jul. 29, 2005, pp. 2665-2672.

United States Patent and Trademark Office, Notice of Allowance, U.S. Appl. No. 11/607,623, Jul. 16, 2010, 8 pages.

United States Patent and Trademark Office, Interview Summary, U.S. Appl. No. 11/606,433, Jun. 14, 2010, 3 pages.

U.S. Appl. No. 11/606,433 Office Action mailed Mar. 10, 2010, 10 pages.

U.S. Appl. No. 11/607,623 Office Action mailed Jan. 12, 2010, 6 pages.

U.S. Appl. No. 11/606,433 Office Action mailed Nov. 15, 2010, 7 pages.

U.S. Appl. No. 11/606,433 Office Action mailed Jul. 28, 2010, 14 pages.

U.S. Appl. No. 12/832,306 Office Action mailed Oct. 1, 2010, 8 pages.

* cited by examiner

- Background, such as air or other gas used to distend colon
- Stool-air interface
- Polyp
- Soft tissue (colon wall)
- Remapped tagged stool Key:
- Greater than +100 HU (Generally rendered white)
- −150 HU to +100 HU (Generally rendered in shades of gray)
- <−150 HU (Generally rendered in black)

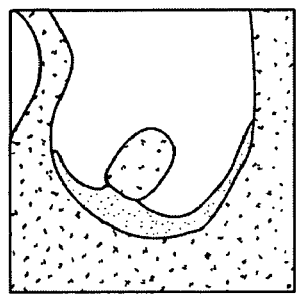
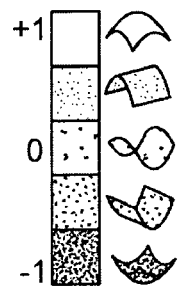
FIG. 5(a)  FIG. 5(b)
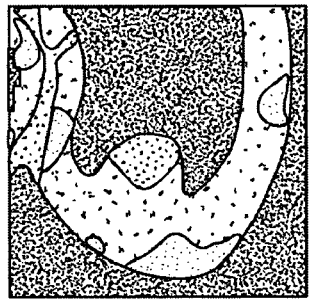
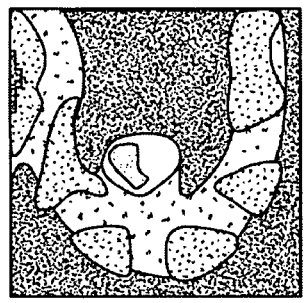
FIG. 5(c)  FIG. 5(d)
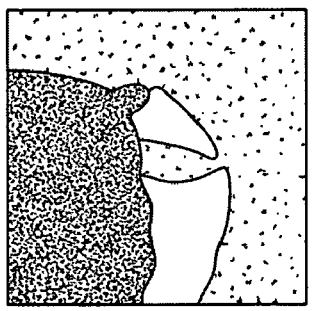
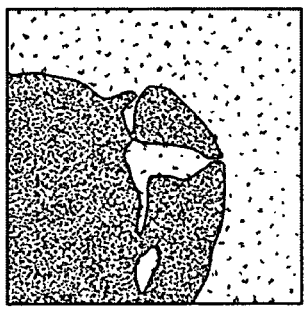
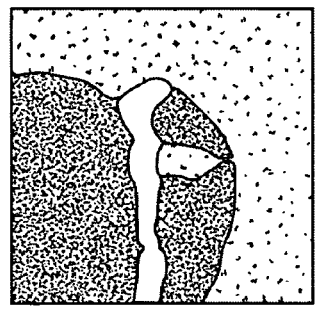
FIG. 6(a)
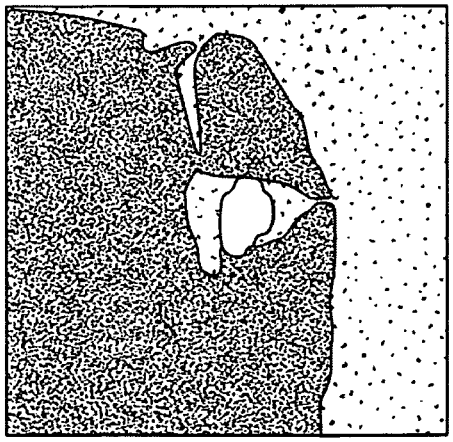
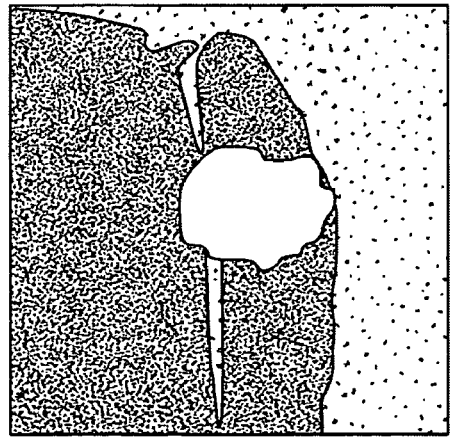
FIG. 6(b)

ADAPTIVE DENSITY MAPPING IN COMPUTED TOMOGRAPHIC IMAGES

RELATED APPLICATIONS

This application is related to U.S. patent application Ser. No. 11/606,443, titled "Adaptive Density Correction in Computed Tomographic Images," filed on Nov. 30, 2006 and U.S. patent application Ser. No. 11/607,623, titled "Lumen Tracking in Computed Tomographic Images," filed on Nov. 30, 2006.

STATEMENT REGARDING FEDERALLY SPONSORED RESEARCH OR DEVELOPMENT

This invention was made with government support under Grant Number CA095279 awarded by the National Cancer Institute. The U.S. Government has certain rights in the invention.

BACKGROUND ART

The present invention relates to computed tomography (CT) and, more particularly, to CT systems that identify interface regions between air and material tagged with contrast agents in CT image data and map CT attenuations of voxels that represent tagged material to CT attenuations that represent air or another gas.

Colorectal cancer is one of the leading causes of cancer-related deaths. Patient screening can reduce colon cancer by facilitating early detection and removal of pre-cancerous polyps. Colonoscopy is considered to have the highest diagnostic performance for screening colon cancer; however, colonoscopy also has a high cost, risk of complications and incidents of patient non-compliance. A minimally invasive alternative procedure, called computed tomography colonography (CTC) or "virtual colonoscopy," is expected to be more cost effective and to involve a lower risk of complications than traditional colonoscopy.

Proper bowl preparation is considered essential for confident detection of colorectal lesions using CTC. This preparation traditionally includes cathartic cleansing of a patient's colon, because residual material in the colon reduces the sensitivity of CTC by imitating polyps. However, cathartic cleansing usually involves administering a laxative. Such cleansings are uncomfortable for the patient, and some residual material remains in the colon, even after such a cleansing. Orally-administered radio-opaque (or high X-ray opacity) contrast agents, such as dilute barium, can be used to opacify residual fluid and stool, so these opacified ("tagged") materials can be identified and distinguished from polyps or other soft tissues. Procedures that use such tagging are commonly referred to as "fecal tagging CTC" (ftCTC).

Interpreting a large number of ftCTC screening cases can be time-consuming for a radiologist, who may grow weary of the task and occasionally miss small polyps or even subtle cancers. Automated image processing ("computer-aided detection" (CAD)) tools can be used to rapidly point out suspicious lesions to radiologists. However, in ftCTC, automated image processing is complicated by an effect commonly known as pseudo-enhancement (PEH), which is an atrifactual increase in the observed X-ray opacity (radio density) of tissues due to the presence of a near-by high radio density tagging agent.

In computed tomography (CT), the internals of an object, such as a human body, are imaged by taking X-ray measurements, yielding data that represents the object as many tightly packed cubes ("voxels"). The radio density of each voxel is calculated by taking the X-ray measurements through the object from a large number of perspectives. A computer digitally processes the X-ray measurements and generates data that represents a three-dimensional model of the object, including the internals of the object. Essentially, the computer "stacks" a series of "slices" of the object to create the model. The data can then be analyzed by a CAD tool. Alternatively or in addition, the data can be used to generate a three-dimensional display or for some other purpose.

The radio density (also called the "CT attenuation" or "CT number") of each voxel is represented by a numeric value along an arbitrary scale (the Hounsfield scale), in which −1,000 represents the radio density of air, and +1,000 represents the radio density of bone. Air causes very little X-ray attenuation and is typically depicted in black on X-ray films, in CT images, etc., whereas bone greatly attenuates X-rays and is typically depicted in white on these films and images. Fat has a radio density of about −120 Hounsfield Units (HU), and muscle has a radio density of about +40 HU. Water is defined as having a radio density of 0 (zero) HU.

Intermediate amounts of CT attenuation are usually depicted by shades of gray in CT images. Because the human eye is unable to distinguish among 2000 shades of grey (representing HU values between +1,000 and −1,000), a radiographer selects a range of CT attenuations that is of interest (i.e., a range of HU values, known as a "window"), and all the CT attenuations within this range are spread over an available gray scale, such as 256 shades of gray. This mapping of a range of CT attenuations to shades of gray is known as "windowing." The center of the range is known as the "window level." Materials having radio densities higher than the top of the window are depicted in white, whereas materials having radio densities lower than the bottom of the window are depicted in black.

Windowing facilitates distinguishing between tissues having similar radio densities. For example, to image an area of a body, such as the mediastinum or the abdomen, in which many tissues have similar radio densities, a narrow range of CT attenuations is selected, and these CT attenuations are spread over the available shades of gray. Consequently, two tissues with only a small difference between their radio densities are ascribed separate shades of gray and can, therefore, be differentiated.

Unfortunately, the tagging in ftCTC affects the calculation of most shape and texture features that are used by CAD systems to identify polyps. Because air has a lower CT attenuation than does soft tissue, and because tagged regions have a higher CT attenuation than do soft tissues, soft-tissue regions covered by tagging are negative image regions, as opposed to soft-tissue regions covered by air. Changes in CT attenuation in such negative images can change the direction of the gradient of CT attenuation and the principal curvature of a local surface. Therefore, shape features that use the principal surface curvature may, for example, indicate that polyps covered by tagged material have concave, rather than the visually perceived convex, shapes. Furthermore, because of the variable effects of tagging, it is not obvious where, how and how much the measured shape and texture features should be adjusted to correct for these effects.

SUMMARY OF THE INVENTION

An embodiment of the present invention provides a method for altering image values of a plurality of voxels. Each of the voxels has a current image value. For each voxel, the method determines if the voxel represents material tagged with a contrast agent. If so, the method sets the image value of the voxel to a value lower than the current image value of the voxel.

Determining whether the voxel represents material tagged with a contrast agent may be done by comparing the image value to a predetermined threshold. If the image value exceeds the predetermined threshold, the voxel is treated as representing material tagged with a contrast agent.

Exemplary thresholds include about 100 HU, about 90 HU, about 110 HU and about 120 HU.

The image value of the voxel may be set according to a predetermined function that is based on the current image value of the voxel.

For a range of current image values, the function may return a range of image values between about the threshold and a lower limit that is different than the threshold, and above the range of current image values, the function may return a single image value.

An exemplary range is about 100 HU to about 200 HU.
An exemplary lower limit is about −1,000 HU.

Above the range, the function may return an image value that represents a gas, such as air, or an image value less than an image of a soft tissue or a fixed value, such as about −1,000 HU.

For the range of current image values, the function may be linear or non-linear.

Optionally, the method may identify an interface between material tagged with a contrast agent and a gas and avoid setting the image value of voxels within the identified interface.

Another embodiment of the present invention provides a method for altering image values of a plurality of voxels. Each voxel has a current image value. For each voxel, the method compares the current image value of the voxel to a predetermined threshold. If the current image value exceeds the predetermined threshold, the image value is set to a value lower than the current image value of the voxel, according to a predetermined scheme.

Image values greater than the predetermined threshold may represent material tagged with a contrast agent, and the image value may be set to an image value that represents a gas.

Yet an embodiment of the present invention provides a method for altering image values of a plurality of voxels. Each voxel has a current image value. The method includes identifying voxels that are within an interface between material tagged with a contrast agent and a gas. For voxels not identified as being within the interface, the method determines if the voxel represents material tagged with a contrast agent. For each voxel that represents material tagged with a contrast agent, the image value of the voxel is set to a value lower than the current image value of the voxel.

Voxels that are within the interface may be identified by a two-step gradient interface analysis.

The first gradient interface analysis step may involve clipping image values according to $v'(p)=\min\{v_1(p), t_T\}$. The second gradient interface analysis step may involve clipping image values according to:

$$v'' = \begin{cases} t_T + 700 & \text{if } v_l(p) \geq t_T \\ v_l(p) & \text{otherwise.} \end{cases}$$

The voxels that are within the interface may be identified according to:

$$A|T = T_{V1'}(t_{V1'}) \cap T_{V1''}(t_{V1''}).$$

BRIEF DESCRIPTION OF THE DRAWINGS

The invention will be more fully understood by referring to the following Detailed Description of Specific Embodiments in conjunction with the Drawings, of which:

FIG. 5 shows an example of the effect of ADM on the calculation of a shape index (SI) feature;

FIG. 6 shows examples CT images with varying applications of ADM;

DETAILED DESCRIPTION OF SPECIFIC EMBODIMENTS

The contents of U.S. Provisional Patent Application No. 60/741,103, filed Nov. 30, 2005, titled "A Method for Computer-Aided Detection of Lesions in Radio-Opaque Contrast Materials," is hereby incorporated by reference herein. In accordance with the present invention, voxels that represent tagged material are altered, such that their CT attenuations represent air or some other low-contrast background, rather than representing a high-contrast tagging agent. Essentially, the CT attenuations of these voxels are mapped to the CT attenuation of air or another background material. Mapping these CT attenuations reduces the effects of tagging on shape and texture features, thus facilitating automatic detection of these shapes and textures and of polyps. Mapping voxels at interfaces between air and tagged material may create artifacts, and these artifacts that may cause false positive (FP) polyp detections. To avoid this problem, some embodiments of the present invention omit voxels that lie within air/tagged material interfaces from automatic polyp detection. These voxels are, however, included in colonic sections that are extracted from CT data as a result of detecting polyps in near-by portions of the colon.

Figure 1:
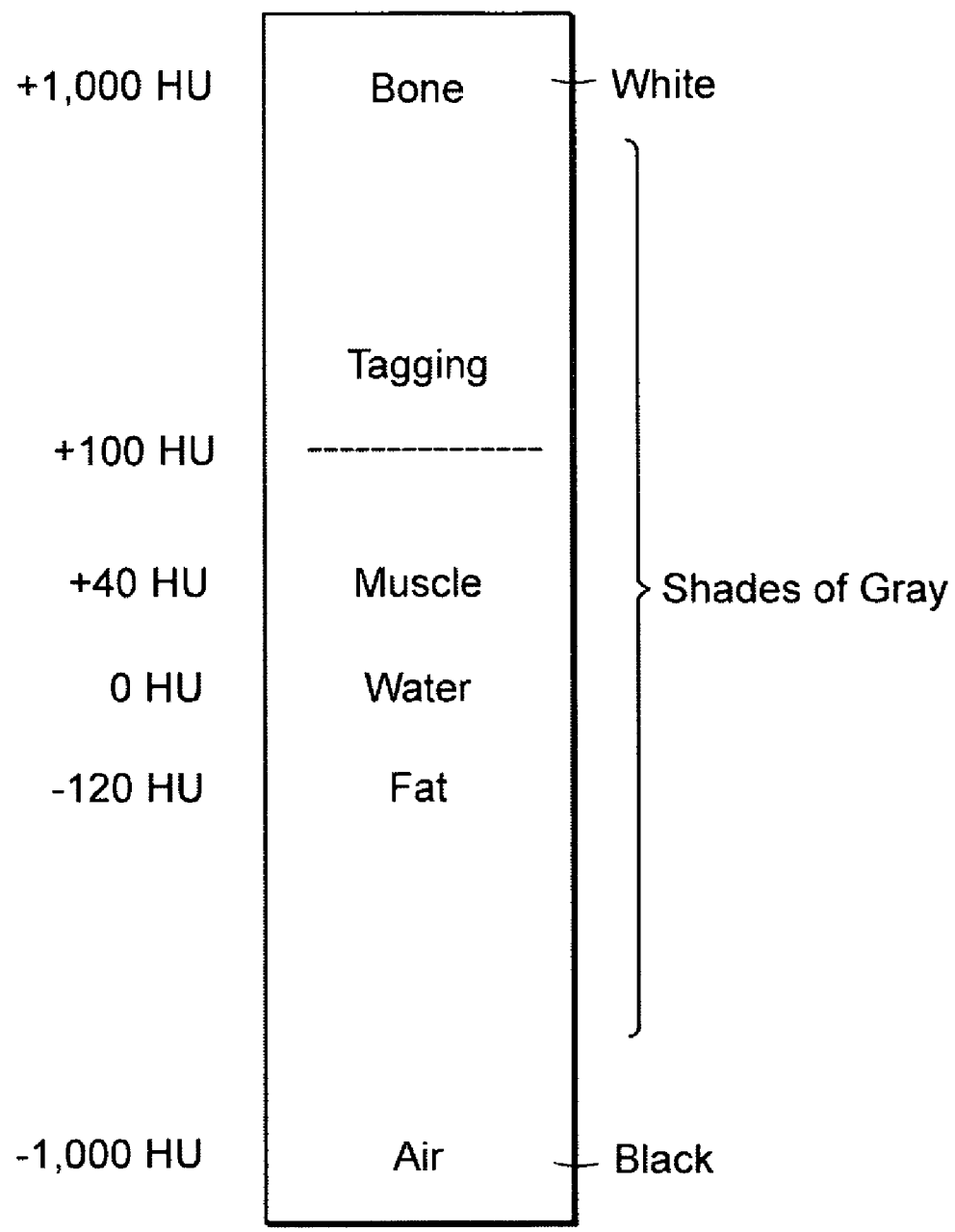
FIG. 1 shows of the Hounsfield scale, along with Hounsfield Unit (HU) values of exemplary materials that may be seen in CT images.

FIG. 1 shows the Hounsfield scale, along with HU values of exemplary materials that may be seen in CT images and indications of how these materials may be depicted in the CT images. For example, bone and tagging material are typically depicted in white; muscle, water, fat and other soft tissues are typically depicted in shades of gray; and air is typically depicted in black.

Figure 2:
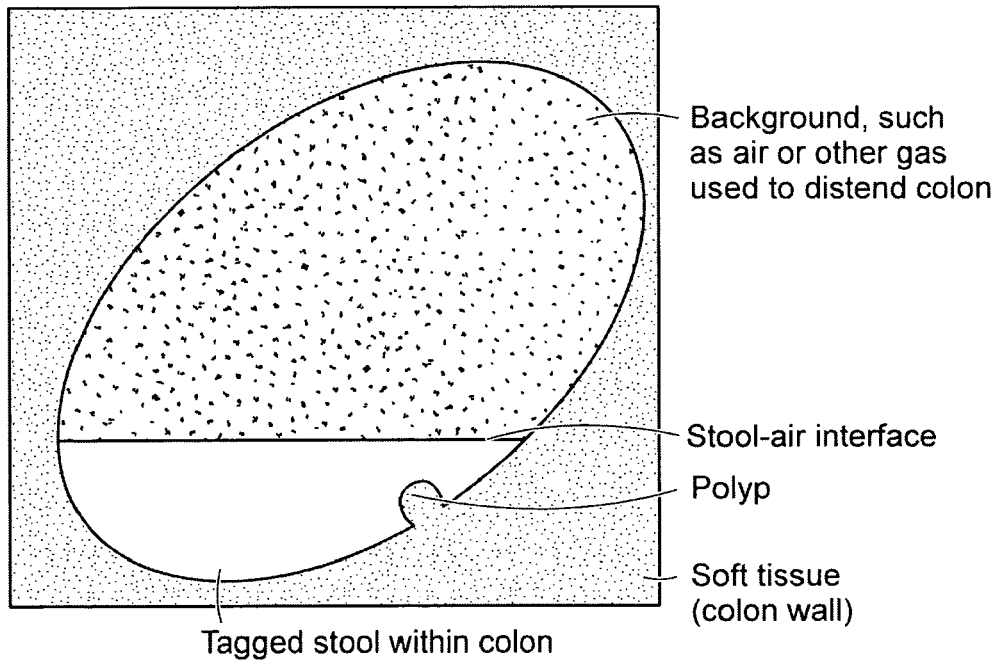
FIG. 2 is an exemplary CT image of a section of a colon that contains tagged fecal material (stool)
Figure 2:
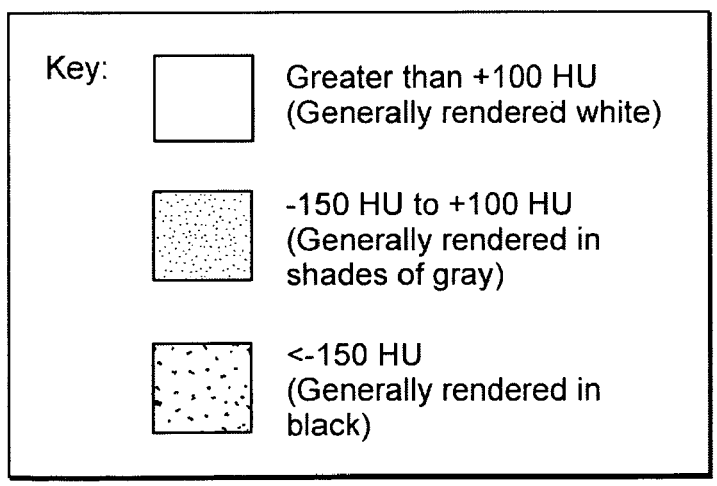

In fecal-tagged CT colonography, opacified residual material exhibits a higher CT attenuation than soft tissues. such as polyps or a colon wall. For example. FIG. 2 is an exemplary CT image of a section of a colon that contains tagged fecal material (stool). Soft tissues, such as the colonic wall and a polyp, have CT values between about −150 HU and about +100 HU; tagged stool has a CT value greater than +100 HU; and background (air) has a CT value less than about 150 HU. The tagged stool is displayed in white, while the colon wall and polyp are displayed in shades of gray. Air or another gas used to distend the colon is displayed in black.

Unfortunately, the contrast between the tagged stool and the soft tissues is opposite the expected contrast. Conventional CAD tools were developed for use with CTC without fecal tagging (referred to herein as "nCTC"). Many of these tools were developed with an assumption that a colon would be cleansed and filled with air or another gas prior to CT imaging. Such automated tools detect polyps according to their shape and depend, at least in part, on expected gradients and contrast between adjacent materials. Consequently, these tools can fail to detect polyps in ftCTC, where residual tagged fecal material is represented by high HU value voxels.

In accordance with one embodiment of the present invention, voxels having CT attenuations greater than a predetermined threshold have their CT attenuations mapped to lower CT values according to a predetermined mapping scheme. For example, voxels having CT attenuations greater than about 100 HU (which typically represents tagged material) are mapped, such that their CT attenuations are about −1,000 HU. Such mapped voxels appear black on CT images, as though they were air. In effect, the tagged material is removed from the CT image and replaced by air. Other thresholds, such as about 90 HU, about 110 HU and about 120 HU can be used.

Figure 3:
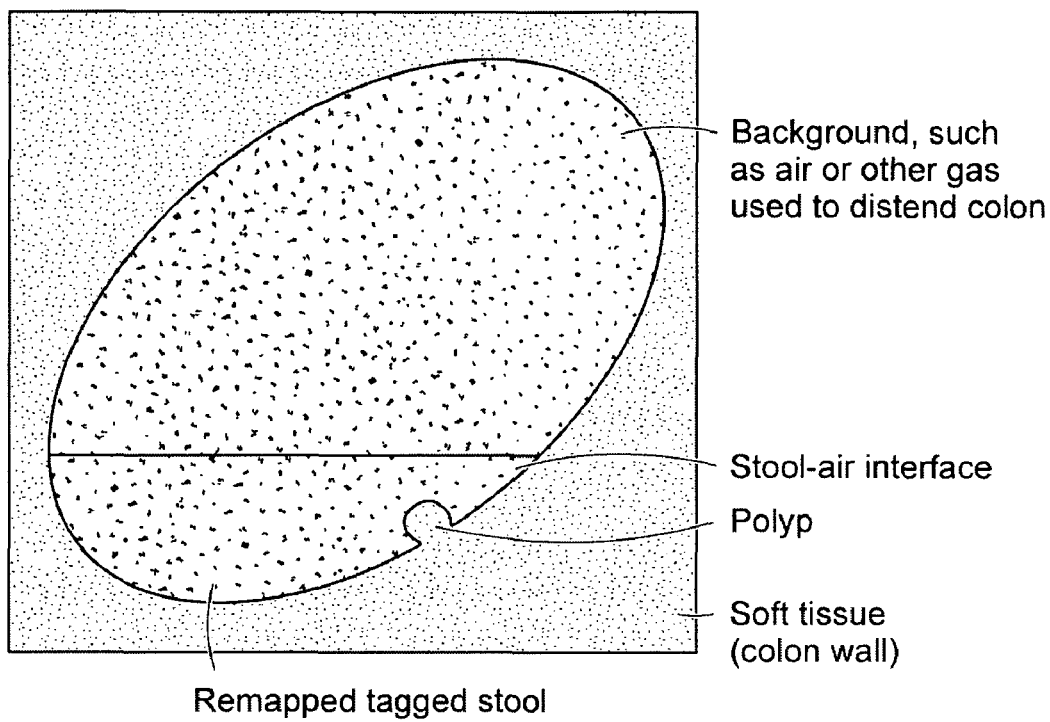
FIG. 3 is the CT image of FIG. 2 after adaptive density mapping (ADM) has been performed, in accordance with one embodiment of the present invention.
Figure 3:
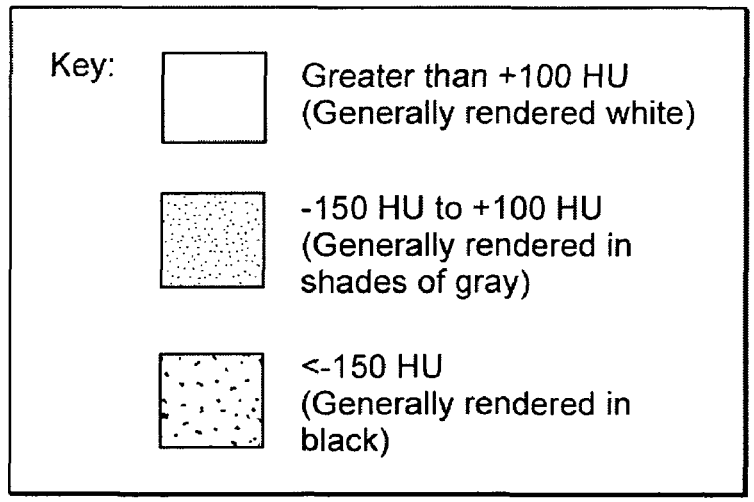

FIG. 3 is the CT image of FIG. 2 after the above-described mapping ("adaptive density mapping" or ADM) has been performed. As can be seen in FIG. 2, the tagged stool is rendered in the same color (black) as the background (such as air or another gas used to distend the colon).

Figure 4:
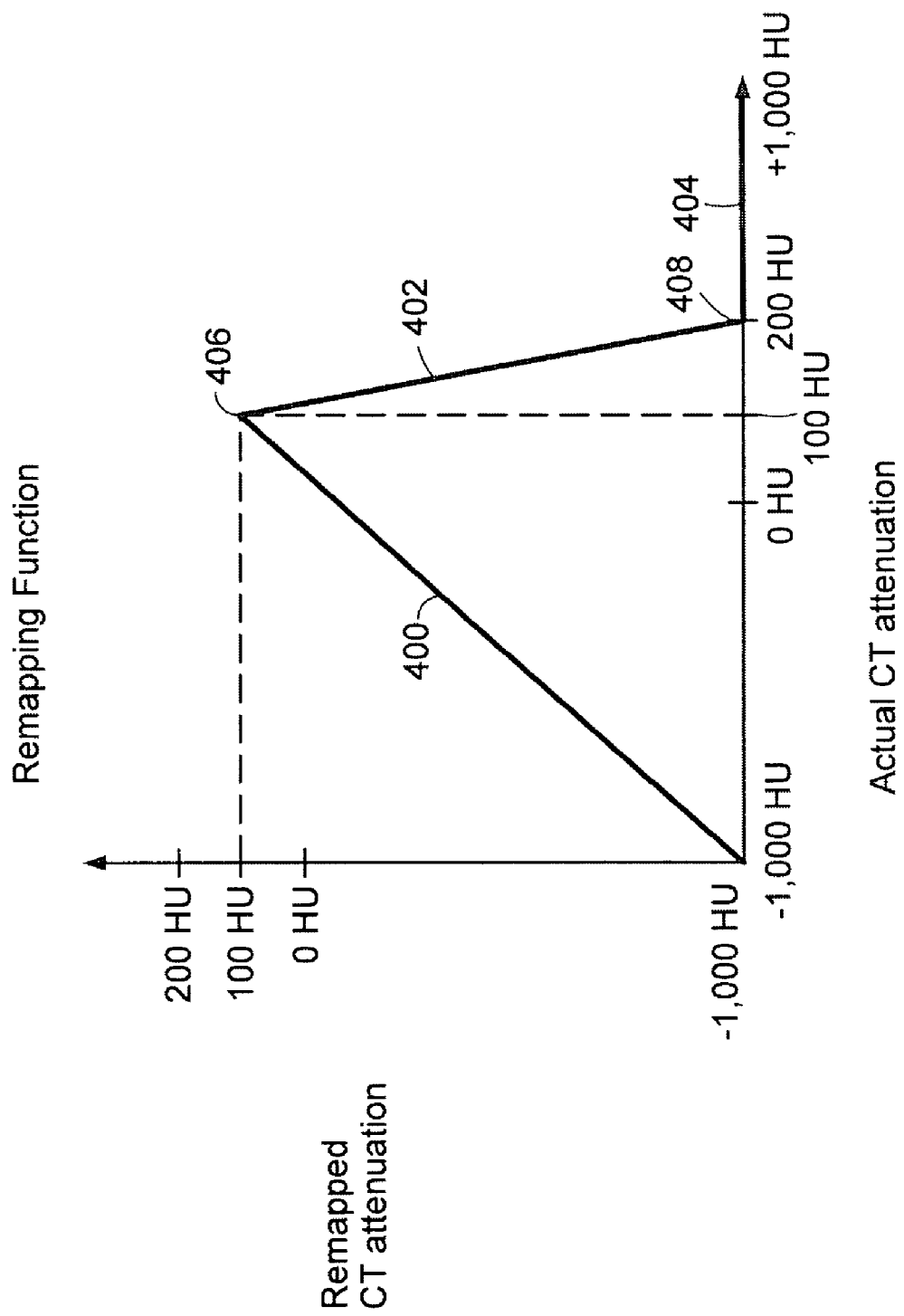
FIG. 4 is a graph of an exemplary mapping function, in accordance with one embodiment of the present invention.

We have found that the mapping function shown graphically in FIG. 4 provides satisfactory results. According to this mapping function, actual CT attenuations between about −1,000 HU and about +100 HU are mapped to themselves, i.e., these CT attenuations are not changed. This portion of the mapping function is represented by an upward-sloped portion 400 of the graph in FIG. 4.

Actual CT attenuations greater than about +100 HU are mapped to CT attenuations that are less than about +100 HU. As shown in a downward-sloped portion 402 of the graph in FIG. 4, CT attenuations between about +100 HU and about +200 HU are linearly mapped to values between about +100 HU and about −1,000 HU. The downward-sloped portion 402 is straight in FIG. 4; however, this portion 402 can be curved or have another shape.

The downward-sloped portion 402 is preferably not vertical (i.e., it does not have a negative infinite slope) to accommodate some uncertainty in identifying the mapped voxels. There is some uncertainty that all voxels that have CT attenuations between about +100 HU and +200 HU represent tagged material. Most, possibly all, of these voxels represent tagged material. It is, however, possible that some of these voxels actually represent soft tissues, such as due to noise in the CT image data, inaccuracies in any adaptive density correction that may have been performed, soft tissues that are actually more dense than expected or for other reasons. This uncertainty decreases as the CT attenuation of a voxel approaches +200 HU. Thus, a non-vertical slope accommodates this uncertainty.

All CT attenuations greater than about +200 HU are mapped to about −1,000 HU, as shown in portion 404 of the graph in FIG. 4. The portion 404 is preferably straight; however, this portion 404 can be curved or have another shape.

Although the dividing point 406 between the first portion 400 and the second portion 402 of the graph, and the dividing point 408 between the second portion 402 and the third portion 404 of the graph are sharp, i.e., the transitions between the respective pairs of portions 400, 402 and 404 are not smooth, other types of transitions are acceptable. For example, these transitions can be smooth curves. More detailed descriptions of a mapping function and interface detection operations follow.

Automated Polyp Detection

The detection of polyps may be based on two volumetric rotation-invariant shape features: a shape index (SI) and a curvedness (CV). The SI characterizes a topologic 3-D shape of a local iso-intensity surface patch in the vicinity of a voxel, and the CV characterizes the flatness of the shape indicated by the SI. Polyp candidates are detected by the application of hysteresis thresholding of the SI and CV features. The complete regions of the detected polyp candidates are extracted by use of conditional morphologic dilation. False positives ("FP") are reduced by applying a Bayesian neural network (BNN), based on shape and texture features calculated from the regions of polyp candidates. The final output of the CAD scheme is determined based on a decision surface generated by the BNN. All of these steps can be fully automated.

Adaptive Density Mapping (ADM)

The purpose of using ADM is to minimize the effect of tagging agents on CT attenuations for automated detection of polyps in ftCTC cases. This allows a uniform calculation of shape and texture features in tagged and untagged regions, without any feature-specific adjustments. ADM includes two steps. In the first step, we identify interface regions between air and tagged materials. In the second step, we convert (map) the CT attenuations to minimize the effects of tagging. For convenient explanation, however, we will describe the second step of ADM before the first step.

CT Attenuation Mapping

Preferably, although not necessarily, the ftCTC data have been preprocessed by an adaptive density correction (ADC) method. Suitable ADC methods and systems are described in co-pending, commonly-assigned U.S. patent application Ser. No. 11/606,443, titled "Adaptive Density Correction of Computed Tomographic Images," filed on Nov. 30, 2006, the contents of which are incorporated by reference herein. Thus, we can assume that CT attenuations $\leq t_T$ represent untagged regions (the establishment of $t_T$ and other parameters is described below and in the above-referenced patent application). Because of the density variation of the observed CT attenuation due to local structural and CT noise and the tagging agent, we also assume that CT attenuations $t_T < v_I < t_U$ can represent both tagged and untagged regions, and that CT attenuations $\geq t_U$ represent only tagged regions. Thus, to minimize the effect of tagging agent, we can map the CT attenuations according to $$\hat{v}_I = \begin{cases} v_I & v_I \leq t_T, \\ t_T - (1000 + t_T)\dfrac{v_I - t_T}{t_U - t_T} & t_T < v_I < t_U, \\ -1000 & v_I \geq t_U. \end{cases} \quad (1)$$

The mapping function defined by Eq. (1) is depicted graphically in FIG. 4.

The mapping does not affect voxels with CT attenuations $\leq t_T$, because these can be assumed to be not affected by tagging after the application of the ADC. The voxels with CT attenuations $\geq t_U$ are assigned the CT attenuation of air (−1,000 HU), because these voxels clearly indicate tagged residual materials that should be ignored. The voxels with CT attenuations between $t_T$ and $t_U$ are mapped linearly from $t_T$ to −1,000 HU, because voxels with CT attenuations close to $t_T$ are more likely to represent soft-tissue regions, whereas voxels with CT attenuations close to $t_U$ are more likely to represent tagged regions.

FIG. 5 shows an example of the effect of ADM on the calculation of the SI feature, which is used for the detection of polyps in our CAD scheme. FIG. 5a shows a polyp covered by tagged fluid. (FIG. 5a provides an axial view of the polyp with a −200+/−800 HU lung display window setting.) FIG. 5b shows the coding between SI values (indicated by a vertical gray-scale bar) and five local surface shapes. The vertical bar indicates the continuous mapping of five discrete local surface example shapes into shape index values. For example, convex cap-like shapes are represented by a white color, whereas concave cup-like shapes are represented by a dark color.

FIG. 5c indicates how the SI values computed from the original CT data of FIG. 5a are reversed under the tagging. FIG. 5c provides a visualization of the values of the shape index within the extracted region of the colonic wall of FIG. 5a. The shapes indicated by the shape index values are mostly opposite to the visually perceived soft-tissue shapes. For example, the convex soft-tissue shape of the polyp is indicated by dark colors that represent a concave shape in the SI coding. FIG. 5d indicates how the SI values have been corrected after the application of ADM. FIG. 5d provides a visualization of the shape index values in the same region after application of ADM. The indicated shapes now match the visually perceived shapes; the region of the polyp is now indicated in white color, which represents a convex shape in the SI coding.

FIG. 6 shows example CT images with varying applications of ADM. FIG. 6a (left) shows a 6 mm polyp located within the surface layer of tagged fluid (in the original CT data). FIG. 6a (middle) shows the effect of application of Eq. (1). In FIG. 6a (right), a white region indicates a transition 6 mm polyp between two materials (air and tagged material) ("A|T") identified by application of a gradient interface analysis ("GIA") method. In FIG. 6b (left), a white region indicates an initially detected region (in the CD data interpolated to isotropic resolution). In FIG. 6b (right), a white region indicates the region of a polyp candidate extracted by conditional morphological dilation.

Air/Tagged Material Interface Identification

Straightforward application of Eq. (1) produces a ridge-like artifact at the interface between air and tagged regions (see FIG. 6). Let A|T denote this interface. The interface A|T represents a transition between two materials (air and tagged materials), the CT attenuation ranges of which are not adjacent to each other on the Hounsfield scale. Therefore, because of the partial-volume effect and the limitations of CT image resolution, it is not obvious whether an observed region of A|T represents a direct transition between air and tagging, or whether A|T represents a transition among air, soft tissue and tagging. Such a problem does not arise with the interface between air and soft tissue (A|S) or with the interface between soft tissue and tagging (S|T), because each of these interfaces represents a continuous transition between two materials whose CT attenuation ranges are adjacent on the Hounsfield scale. Because the interface A|T is typically composed of a variable mixture of air, tagged region and soft-tissue structures (such as polyps, folds or poorly tagged residual materials) and because the interface is also affected by the pseudo-enhancement (PEH) and partial-volume effects of the above materials, it is not obvious how to precisely reconstruct the actual CT attenuations at A|T. Furthermore, errors in such a reconstruction can easily produce polyp-like artifacts that increase the number of false positive (FP) CAD detections.

To avoid FPs from being introduced by the interface A|T during the detection of polyp candidates, we first identify A|T and then exclude the voxels within A|T from the detection. In particular, we do not modify A|T but keep the CT attenuations within A|T intact in order to avoid reconstruction artifacts and errors from being introduced in the calculation of volumetric shape features that are used for the detection. However, after detecting polyp candidates, we omit this constraint on the interface A|T. Thus, when the complete region of the polyp candidates is extracted by use of conditional morphological dilation, the extracted region is allowed to include voxels from A|T. Therefore, although any FP CAD detections that could originate from A|T will be excluded, the complete region of the detected polyp candidates is extracted. The polyps that are of clinical interest are greater than 6 mm, and they are large enough to remain detectable by CAD, even if they are located at A|T.

To identify A|T, we first identify the regions of air (A), tagging (T), and soft tissue (S). FIG. 8 contains two exemplary graphs showing of three different interface types in phantom data with 300 HU tagging during the (a) first and (b) second step of a two-step gradient interface analysis (GIA). The data were preprocessed by the ADC method. In (a), CT attenuations greater than 100 HU have been clipped to 100 HU. The contrast between soft tissue and tagging is much lower than that between the other interfaces. In (b), CT attenuations greater than 100 HU have been clipped to 800 HU. The contrast between air and soft tissue is much lower than that between air and tagging. Based on these data, the three interfaces may be differentiated, as explained below.

Figure 8A:
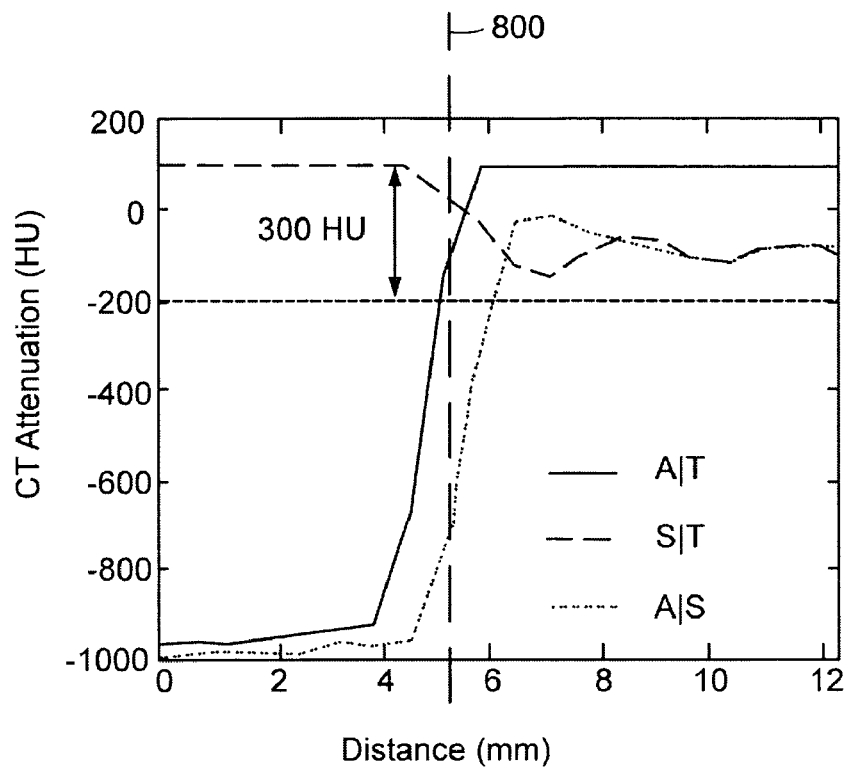
FIG. 8 contains two exemplary graphs of CT attenuations at various interfaces.
Figure 8B:
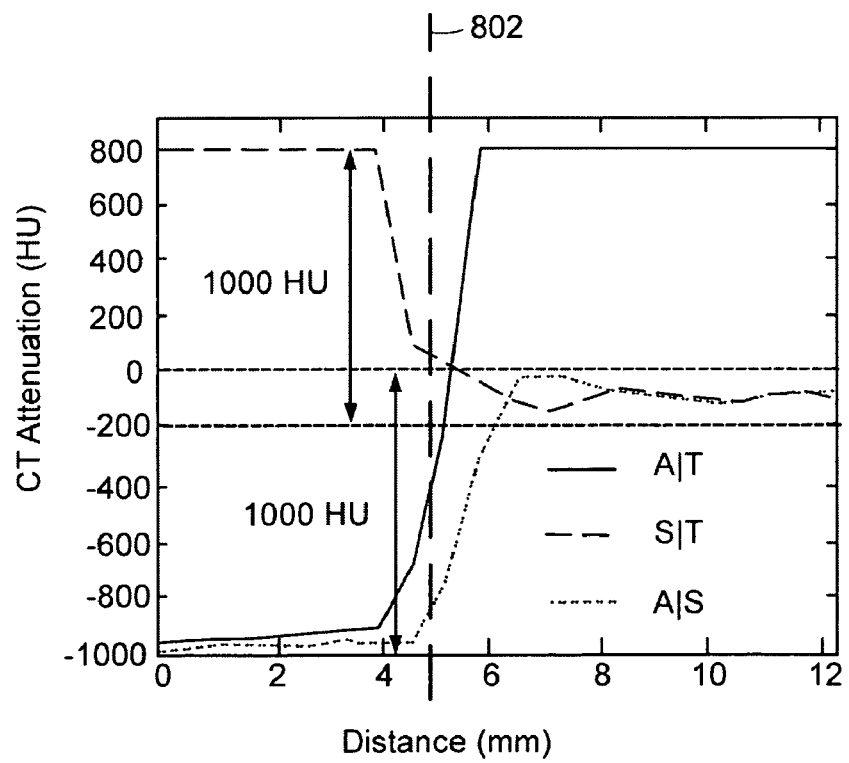

The interface regions A|T, A|S and S|T are identified by the two-step gradient GIA. FIG. 8 contains profile graphs of these interfaces after the first step (FIG. 8a) and after the second step (FIG. 8b) have been performed. The interface can be thought of as a vertical line or region, approximately as shown by vertical dashed lines 800 and 802. The solid, dashed and light plot lines indicate CT attenuations at various distances, relative to the interfaces 800 and 802. Thus, for example in FIG. 8a, the solid line plots CT attenuations for the A|T interface. As can be seen from the plot, on one side (i.e., the air side) of the interface 800, the CT attenuations are very low, near −1,000 HU. On the other side (i.e, the tagged material side) of the interface 800, the CT attenuations are high. The difference between CT attenuations on one side of the interface 800 and the other side of the interface 800 is referred to as a "contrast." Thus, the A|T interface has a high contrast.

The first step of the GIA involves clipping all CT attenuations at a predetermined value, such as 100 HU. The result of this clipping is shown in FIG. 8a. This clipping brings the three plots close together on the tagged side of the interface. As can be seen from FIG. 8a, the A|T and the A|S interfaces have higher contrasts than the S|T interface. Thus, the S|T interface can be distinguished from the other two interfaces.

The second step of the GIA uses the original CT image data, i.e., the second step does not use the results of the first step. The second step involves identifying voxels that have actual CT attenuations greater than 100 HU and setting the CT attenuations of these voxels to a predetermined value, such as 800 HU. This operation is referred to as "stretching." The result of this step is shown in FIG. 8b. As can be seen from FIG. 8b, this stretching forces the A|T interface away from the other two interfaces, thus the A|T interface has a higher contrast than the other two interfaces, and the A|T interface can be distinguished from the other two interfaces.

Essentially, the original CT image data is fed in parallel to two transforms. One transform identifies the S|T interface, and the other transform identifies the A|T interface. Now, being able to distinguish the S|T and the A|T interfaces, we can distinguish the A|S interface. These operations are described in more detail below.

Let $T_1(n)$ denote the binary region obtained by thresholding I at a CT attenuation n:

$$v_{T_1(n)}(p) = \begin{cases} 1 & \text{if } v_I(p) \geq n, \\ 0 & \text{otherwise.} \end{cases} \quad (2)$$

Let $\neg T_{1(n)}(p)$ denote the negation of $T_{1(n)}(p)$: if $v_{T_1(n)}(p)=m$ (m=0, 1), then $v\neg_{T_1(n)}(p)=1-m$. Let parameter $t_A$ denote the highest CT attenuation that represents air ($t_A=-700$). Then, the region of air is represented by $A=\neg T_1(t_A)$, the tagged region is represented by $T=T_1(t_T)$, and the soft-tissue region is represented by $S=\neg T_1(t_T) \cap T_1(t_A)$.

Figure 7:
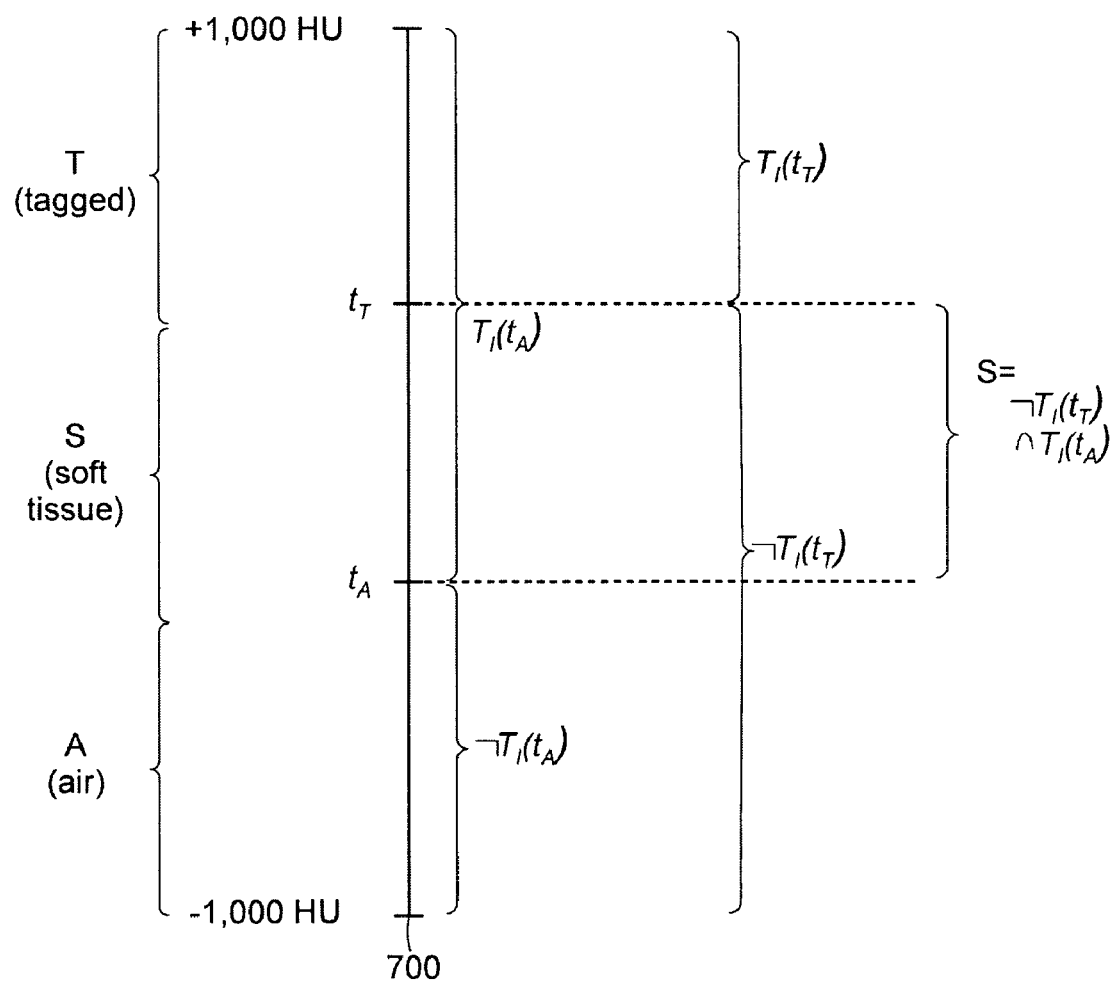
FIG. 7 is a schematic illustration of interface identification, in accordance with one embodiment of the present invention.

This identification process is depicted graphically in FIG. 7, which includes a Hounsfield scale 700. Along this scale 700, $t_A$ denotes the highest CT attenuation that represents air, and $t_r$ denotes the highest CT attenuation less than tagged material. Thus, the region of air is represented by $A=\neg T_1(t_A)$, and the tagged region is represented by $T=T_1(t_T)$. The region of soft tissue is represented by an intersection of the region that is not air (i.e., $\neg T_1(t_T)$) with the region that is not tagged (i.e., $T_1(t_T)$).

The interface regions are identified by use of a two-step gradient interface analysis (GIA). In the first step of the GIA, the CT attenuations of I are clipped according to $v'(p)=\min\{v_1(p),t_T\}$. Let I' denote the resulting clipped data, and let $\nabla I$ denote the gradient of the input data I. Then, the interfaces A|S and A|T can be determined by the calculation of $A|T \cup A|S = T_{\nabla I'}(t_{\nabla I'})$, where $t_{\nabla I'}$ is set to exceed the highest contrast of the CT attenuation within the interface S|T (see also FIG. 8a). Therefore, $S|T \nsubseteq A|T \cup A|S$.

In the second step of the GIA, we clip the CT attenuations of I according to $$v''(p) = \begin{cases} t_T + 700 & \text{if } v_I(p) \geq t_T \\ v_I(p) & \text{otherwise} \end{cases} \quad (3)$$

Let I" denote the resulting data. The contrast between A and T in I", and that between S and T, is now higher than the contrast between A and S (see also FIG. 8b). Consequently, we can differentiate among the three interfaces as follows:

$$A|T = T_{\nabla I''}(t_{\nabla I''}) \cap T_{\nabla I'}(t_{\nabla I'}) \quad (4)$$

$$A|S = T_{\nabla I'}(t_{\nabla I'}) \setminus T_{\nabla I''}(t_{\nabla I''}) \quad (5)$$

$$S|T = T_{\nabla I''}(t_{\nabla I''}) \setminus T_{\nabla I'}(t_{\nabla I'}) \quad (6)$$

where $t_{\nabla I''}$ is set to exceed the highest contrast of the CT attenuation within the interfaces A|S and S|T. Thus, we have obtained the region of the interface A|T, which is then excluded from the detection of polyp candidates, as explained above.

Parameter Estimation

For parameter optimization, an anthropomorphic human-colon phantom (Phantom Laboratory, Salem, N.Y., USA) was filled partially with three different concentrations of an iodine-based tagging agent (Oxilan, Guerbet, Bloomington, Ind., USA). The materials of the phantom had been designed to resemble features observed in human CTC scans. In particular, the CT attenuations of soft-tissue structures were less than 100 HU. The phantom was scanned by use of a four-channel CT scanner (LightSpeed, GE Medical Systems, Milwaukee, Wis., USA) with CT parameters similar to those used routinely with clinical cases at our institution: 3.75 mm collimation, a 1.8 mm reconstruction interval, and a 50 mA current with 140 kVp voltage. The three resulting CT scans represented the phantom with uniform taggings of retained fluid at 300 HU, 600 HU, and 900 HU.

The ADC method was optimized to reduce the maximum CT attenuation within pseudo-enhanced soft-tissue regions to less than 100 HU simultaneously in all three phantom scans. The optimization of the ADC method is described in detail in the above-referenced patent application. In particular, the optimization involves the estimation of the parameter function $\sigma_2$. The resulting function generates a large correction (Gaussian spread) for high levels of residual energy and a small correction for low levels of residual energy. Thus, when the ADC method is applied to a CT scan volume that has variable tagging density levels in different regions of the colon, the pseudo-enhancement is corrected adaptively at each local region.

The ADM method has two key parameters: $t_T$ and $t_U$ (see Eq. (1)). For compatibility with the ADC method, we set $t_T=100$ HU. This value is also in agreement with the range of the Hounsfield scale for soft-tissue structures. To determine a suitable value for $t_U$ we observed that previous experimental clinical studies had indicated tagged regions by use of CT attenuation thresholds from 150 HU to 200 HU. To investigate the effect of tagging density in our CAD scheme, we preprocessed the phantom ftCTC data with the optimized ADC method and calculated line samples through 11 simulated polyps 8-18 mm that were fully covered by tagged fluid.

Figure 9:
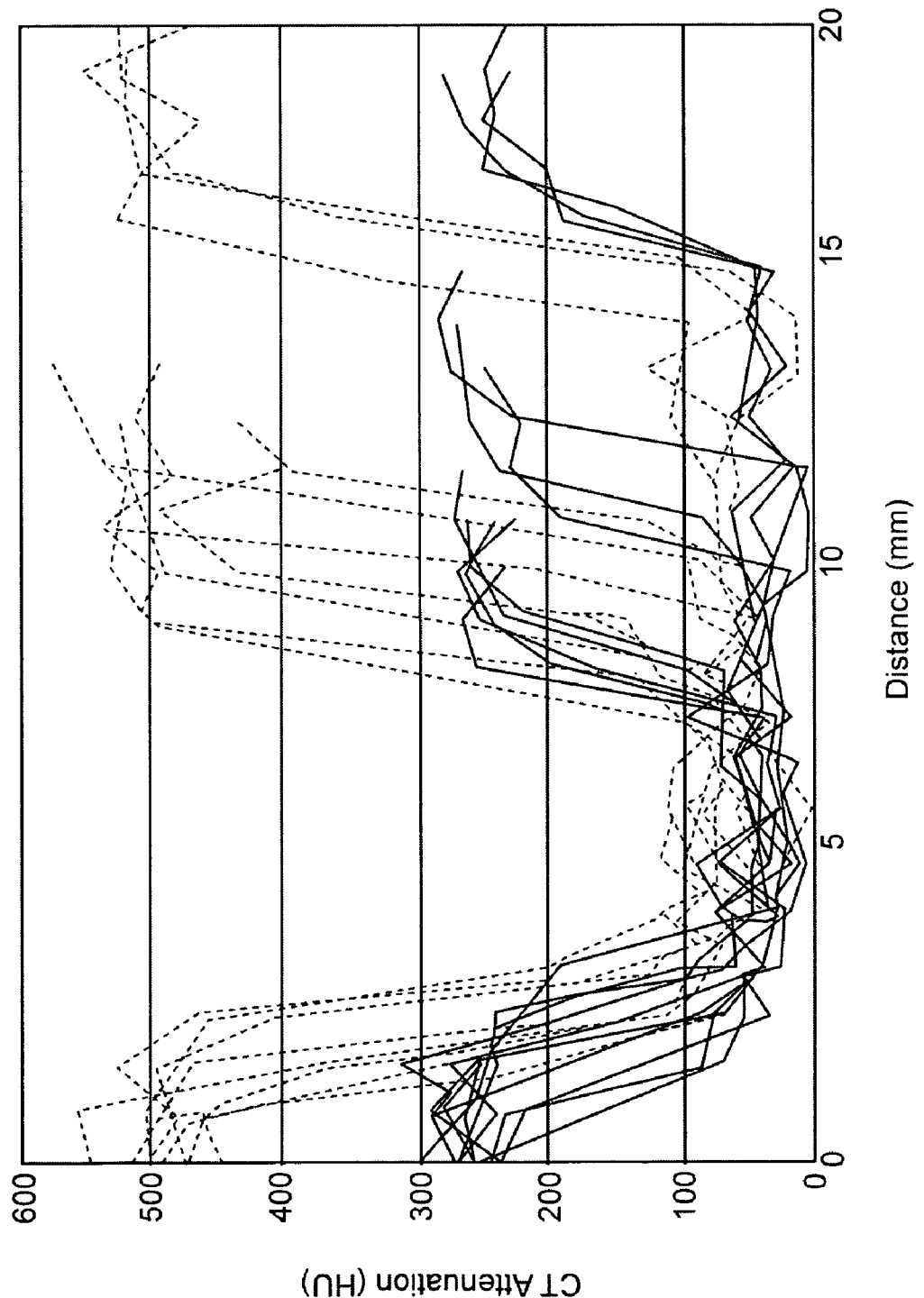
FIG. 9 shows examples of line-sample plots through simulated polyps.

FIG. 9 shows examples of the line-sample plots through simulated polyps. The solid lines indicate samples at the 300 HU tagging level, and the dotted lines indicate samples at the 600 HU tagging level. As can be seen from the plots, the CT attenuation within the polyps is mostly less than 100 HU after application of the ADC. The plots also indicate that CT attenuations greater than 200 HU are generally associated with tagging, whereas CT attenuations within 100-200 HU represent a transition between soft tissue and tagged materials. Therefore, we set $t_U=200$ HU.

The parameter values of the GIA method were estimated similarly as above by use of the phantom data and the Hounsfield scale. We estimated the threshold $t_{\nabla I'}=300$ for differentiating the interface S|T from the interfaces A|S and A|T by studying the line samples of these interface regions in the phantom (FIG. 8a). Because the CT attenuations greater than 100 HU were clipped to 100 HU, the gradient of the CT attenuation is less than 300 HU at S|T. The threshold $t_{\nabla I''}=t_{\nabla I'}+700$ for differentiating between A|T and A|S was estimated similarly (FIG. 8b): because the CT attenuations greater than 100 HU were clipped to 800 HU, the interface A|T has a higher gradient than does interface A|S. Conservative threshold values were chosen to accommodate the limited image resolution and the structural and CT imaging noise of clinical cases.

Where applicable, detection parameters previously used in nCAD may be used in ftCAD. Furthermore, although an embodiment of the present invention has been described that first identifies an interface region between air and tagged material, then maps CT attenuations of voxels that are not in the interface region, other embodiments perform the mapping without identifying such an interface region. Yet other embodiments identify such an interface region without mapping CT attenuations. Thus, disclosed methods and systems can be used in combination or separately.

A system for implementing the above-described adaptive density mapping may be implemented by a computer executing instructions stored in a memory. Input data, such as CT values of voxels in a CT scan of a human being, can be provided from a CT system to the above-described computer, or the above-described computer can be integrated into the CT system. In common practice, CT data is received from a CT system and stored in a picture archiving and communication system (PACS). This data can be used by the above-described computer to perform ADM, such as in a preprocessing step prior to CAD.

Some of the functions performed by the ADM system and method have been described with reference to flowcharts. Those skilled in the art should readily appreciate that functions, operations, decisions, etc. of all or a portion of each block, or a combination of blocks, of the flowcharts can be implemented as computer program instructions, software, hardware, firmware or combinations thereof. Those skilled in the art should also readily appreciate that instructions or programs defining the functions of the present invention can be delivered to a processor in many forms, including, but not limited to, information permanently stored on non-writable storage media (e.g. read only memory devices within a computer, such as ROM, or devices readable by a computer I/O attachment, such as CD-ROM disks), information alterably stored on writable storage media (e.g. floppy disks and hard drives) or information conveyed to a computer through communication media, including computer networks. In addition, while the invention may be embodied in software, the functions necessary to implement the invention may alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. Moreover, while the preferred embodiments are described in connection with CT data, one skilled in the art will recognize that the system may be embodied using data from a variety of image systems, such as magnetic resonance imaging (MRI), X-ray, ultrasound and the like. Furthermore, subsets, combinations and subcombinations of the described systems and methods can be used alone or with other systems. Accordingly, the invention should not be viewed as limited, except by the scope and spirit of the appended claims.

What is claimed is:

1. A method for altering image values of a plurality of voxels, each of the voxels having a current image value, the method comprising:
    for each voxel, determining if the voxel represents material tagged with a contrast agent;
    identifying an interface between material tagged with a contrast a contrast agent and a gas; and
    for each voxel that represents material tagged with a contrast agent, but that is not within the identified interface, setting the image value of the voxel to a value lower than the current image value of the voxel.

2. A method for altering image values of a plurality of voxels, each voxel having a current image value, the method comprising:
    identifying voxels that are within an interface between material tagged with a contrast agent and a gas; and
    for voxels not identified as being within the interface:
        determining if the voxel represents material tagged with a contrast agent; and
        for each voxel that represents material tagged with a contrast agent, setting the image value of the voxel to a value lower than the current image value of the voxel.

3. A method according to claim 2, wherein identifying voxels that are within the interface comprises a two-step gradient interface analysis.

4. A method according to claim 3, wherein:
    the first gradient interface analysis step comprises clipping image values according to:

$v'(p) = \min\{v_I(p), t_T\}$; and the second gradient interface analysis step comprises clipping image values according to:

$$v''(p) = \begin{cases} t_T + 700 & \text{if } v_I(p) \geq t_T \\ v_I(p) & \text{otherwise.} \end{cases}$$

5. A method according to claim 2, wherein the voxels that are within the interface are identified according to:

$A|T = T_{\nabla I'}(t_{\nabla I'}) \cap T_{\nabla I''}(t_{\nabla I''})$.

6. A system for altering image values of a plurality of voxels, each of the voxels having a current image value, comprising:
    a computer programmed to:
        for each voxel, determine if the voxel represents material tagged with a contrast agent;
        identify an interface between material tagged with a contrast agent and a gas; and
        for each voxel that represents material tagged with a contrast agent, but that is not within the interface, set the image value of the voxel to a value lower than the current image value of the voxel.

7. A computer program product, comprising:
    a non-transitory computer-readable medium on which is stored computer instructions for:
        for each voxel, determining if the voxel represents material tagged with a contrast agent;
        identifying an interface between material tagged with a contrast agent and a gas; and
        for each voxel that represents material tagged with a contrast agent, but that is not within the interface, setting the image value of the voxel to a value lower than the current image value of the voxel.

* * * * *